(12) United States Patent
Hall et al.

(10) Patent No.: US 9,238,078 B2
(45) Date of Patent: Jan. 19, 2016

(54) MODIFIED-RELEASE PHARMACEUTICAL DRUG COMPOSITION

(75) Inventors: Harlan Hall, Oregon, WI (US); J. Scott Madsen, Cottage Grove, WI (US)

(73) Assignee: Coating Place, Inc., Verona, WI (US)

( * ) Notice: Subject to any disclaimer, the term of this patent is extended or adjusted under 35 U.S.C. 154(b) by 0 days.

(21) Appl. No.: 13/262,687

(22) PCT Filed: Apr. 1, 2010

(86) PCT No.: PCT/US2010/029652
§ 371 (c)(1),
(2), (4) Date: Dec. 2, 2011

(87) PCT Pub. No.: WO2010/115015
PCT Pub. Date: Oct. 7, 2010

(65) Prior Publication Data
US 2012/0064167 A1    Mar. 15, 2012

Related U.S. Application Data (60) Provisional application No. 61/275,697, filed on Apr. 3, 2009.

(51) Int. Cl.
| | |
|---|---|
| *A61K 9/16* | (2006.01) |
| *A61K 47/48* | (2006.01) |
| *A61K 9/00* | (2006.01) |
| *A61K 9/14* | (2006.01) |
| *A61K 9/50* | (2006.01) |
| *A61K 31/137* | (2006.01) |
| *A61K 45/06* | (2006.01) |
| *A61K 31/192* | (2006.01) |

(52) U.S. Cl.
CPC ......... *A61K 47/48184* (2013.01); *A61K 9/0095* (2013.01); *A61K 9/146* (2013.01); *A61K 9/5047* (2013.01); *A61K 31/137* (2013.01); *A61K 31/192* (2013.01); *A61K 45/06* (2013.01)

(58) Field of Classification Search
CPC ... A61K 9/0095; A61K 9/146; A61K 9/5047; A61K 31/137; A61K 31/192; A61K 45/06; A61K 47/48184; A61K 2300/00
See application file for complete search history.

(56) References Cited

U.S. PATENT DOCUMENTS

| | | | |
|---|---|---|---|
| 4,221,778 A | 9/1980 | Raghunathan | |
| 6,211,246 B1 | 4/2001 | Gelotte et al. | |
| 7,060,730 B2 | 6/2006 | Gelotte et al. | |
| 7,871,645 B2 * | 1/2011 | Hall et al. | 424/490 |
| 2004/0091508 A1 | 5/2004 | Gelotte et al. | |
| 2005/0266032 A1* | 12/2005 | Srinivasan et al. | 424/400 |
| 2007/0059270 A1* | 3/2007 | Hall et al. | 424/78.1 |

FOREIGN PATENT DOCUMENTS

| | | |
|---|---|---|
| EP | 0 171 528 A2 | 2/1986 |
| EP | 0 565 301 A1 | 10/1993 |
| EP | 0 911 039 A2 | 4/1999 |
| WO | WO 92/10171 | 6/1992 |
| WO | WO 98/27961 | 7/1998 |
| WO | WO 03/020242 A1 | 3/2003 |

* cited by examiner

*Primary Examiner* — Johann R Richter
*Assistant Examiner* — David Browe
(74) *Attorney, Agent, or Firm* — McCarter & English, LLP; Steven G. Davis; Wei Song (57) ABSTRACT

The present invention provides compositions and methods for a modified-release pharmaceutical drug composition having a first charged active agent and a second charged active agent at least partially surrounded by a rate controlling membrane. The first charged active agent and the second charged active agent interact to form a modified release pharmaceutical complex within the rate controlling membrane and the modified release pharmaceutical complex has a release characteristic different from the release characteristic of the first active agent or the second active agent alone.

6 Claims, 1 Drawing Sheet

Storage Stability of Phenyl Release in Compounded Syrup (Prep'd Dec 06)

MODIFIED-RELEASE PHARMACEUTICAL DRUG COMPOSITION

CROSS REFERENCE TO RELATED APPLICATIONS

Related Applications

This application is a 35 U.S.C. §371 national stage filing of International Application No. PCT/US2010/029652, filed Apr. 1, 2010, which claims priority under 35 U.S.C. §119(e) to U.S. Provisional Application Ser. No. 61/275,697, filed Apr. 3, 2009. The entire contents of each of the aforementioned applications are incorporated herein by reference in their entirety.

TECHNICAL FIELD OF THE INVENTION

The present invention relates in general to the field of the modified release of active agents, and in particular, to pharmacologically active drugs adsorbed to ion exchange resins.

BACKGROUND OF THE INVENTION

Combination therapies are often used to treat various diseases and conditions. Administering the combination to the patient in a single formulation is more convenient and improves patient compliance. However, administering two pharmaceutically active agents in a single dose is problematic if one of the agents is metabolized more rapidly than the second. Because the dosing regimen will be determined by the agent that is cleared more slowly, the pharmaceutical effect of the more rapidly cleared agent will be absent for a period of time after it is cleared until it is time to re-administer the combination.

This problem could be addressed if the single formulation contains a controlled release composition that comprises the more rapidly metabolizing agent. However, the second more rapidly clearing agent may adversely effect the release profile of the controlled release composition of the first agent. For example, this can occur in liquid formulations when the two pharmaceutically active agents are charged moieties of opposite charge.

Advil Cold and Sinus™ is one example. This combination product contains the decongestant pseudoephedrine and ibuprofen in a syrup. Pseudoephedrine is far more rapidly hydrolyzed than ibuprofen. Although controlled release formulations of pseudoephedrine can be prepared, their release profile is often altered in the presence of ibuprofen.

Therefore, improved pharmaceutical formulations for combination therapies are needed.

SUMMARY OF THE INVENTION

Disclosed herein are compositions and methods for combination therapies comprising two oppositely charged drugs or active agents that overcome the aforementioned problems. The active agent-ion exchange resin compositions disclosed herein contain a first charged active agent equilibrated to the resin particles and then a second charged active agent coated onto the first active agent-resin particles. This composition is then coated with a rate controlling membrane and is optionally suspended in a liquid or a syrup containing the second charged active agent. It is unexpectedly found that this composition containing the first active agent and the second active agent inside the rate controlling membrane, is a controlled release formulation at least with respect to the first active agent.

Accordingly, there is provided a method of preparing a controlled release active agent-ion exchange resin composition, by loading an ion exchange resin with a first charged active agent to result in an active agent-ion exchange resin; and coating the active agent-ion exchange resin with a second charged active agent.

In another aspect, there is provided a controlled release composition, comprising a first charged active agent and a second charged active agent, wherein the second charged active agent is of an opposite charge than the first charged active agent, and wherein the first charged active agent and the second charged active agent are coated with a rate controlling membrane.

The present inventors recognized active agent release profiles can be affected by interactions between ionic or charged molecule pairs. These oppositely charged ions form an attraction between the positively-charged end of one molecule and the negative end of another or the same molecule.

The present inventors further recognized that one of the key parameters is that two compounds develop opposite charges within their respective molecules and that the attraction of these differing charges causes mutual attraction. For example, the present inventors recognized that in one example, one compound has a locus of negative charges (e.g., carboxyl group) and the other has a locus of positive charges (e.g., amine). For example, the phenylephrine exhibits faster absorption when complexed with ibuprofen, such complex forming spontaneously when both compounds are present in a liquid formulation. Another example of this effect is the stability and/or altered solubility when complexed with appropriate paired compounds, such complex being formed and isolated prior to combining into a formulated dosage form.

It was found that controlled release profiles may be manipulated by complexing ion exchange resins and drug compounds followed by coating with a semi-permeable film that modulates the availability of competing compounds. In some embodiments, the coating of the second drug onto the drug-ion exchange resin results in a formation of a drug/drug complex. The present inventors establish that when such drug/drug complexes can form they compete with the drug-ion exchange resin or the compound/ion resin complexes and change the release profile relative to that observed when the second drug is not present.

In some embodiments, there is provided a modified-release pharmaceutical drug composition including a first charged active agent and a second charged active agent at least partially surrounded or completely surrounded or encapsulated by a rate controlling membrane. The first charged active agent and the second charged active agent interact to form a modified release pharmaceutical complex within the rate controlling membrane wherein the modified release pharmaceutical complex has a release characteristic different from the release characteristic of the first active agent or the second active agent alone.

The present invention also provides a method of preparing a modified-release pharmaceutical drug composition by combining a first charged active agent and a second charged active agent to form a modified release pharmaceutical complex with a release characteristic different from the release characteristic of the first active agent or the second active agent alone and coating the modified release pharmaceutical complex with a rate controlling membrane, wherein the modified release pharmaceutical complex is formed within the rate controlling membrane.

The present invention also provides a modified-release pharmaceutical drug-ion exchange resin composition including a pharmaceutical drug complex loaded onto an ion exchange resin. The pharmaceutical drug complex includes a first charged active agent in contact with a second charged active agent. The first active agent and the second active agent interact to form a modified release complex in which the first active agent, the second active agent or both have a release characteristic that are modified in a manner different than that achieved when the ion exchange resin is not used.

The present invention provides a method of modifying the release characteristics of a pharmaceutical drug-ion exchange resin composition by contacting a modified release complex with an ion exchange resin. The modified release complex comprises a first charged active agent and a second charged active agent, wherein the modified release complex has release characteristics that are different than that achieved when the ion exchange resin is not used

DETAILED DESCRIPTION OF THE INVENTION

Figure 1:
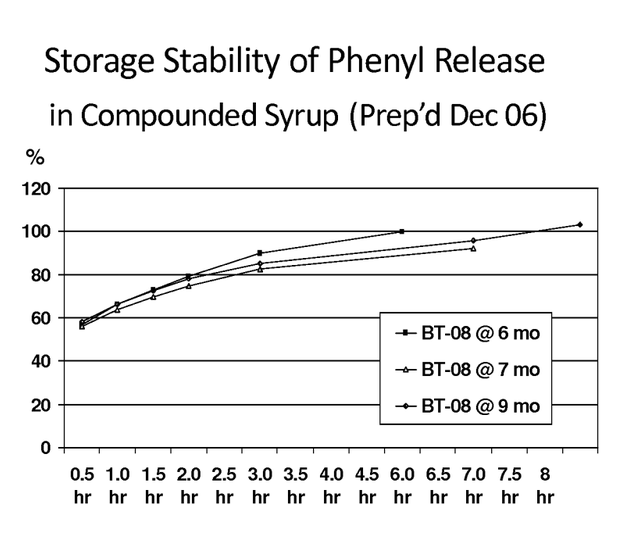
FIGURE is a graph showing percent release of phenylephrine from a controlled release formulation of the invention over time in hours after storage for 6 months, seven months and eight months, measured using an ASP Apparatus 2. The controlled release formulation is the coated phenylephine/ion exchange resin complex described in the exemplification and is suspended in syrup. Ibuprofen is suspended in the syrup and ionically bonded to the phenylephrine.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A number of definitions are provided herein to facilitate an understanding of the present invention. As used herein, the term "pharmaceutical composition" also means a solution, suspension, cream, ointment, lotion, capsule, caplet, softgel, gelcap, suppository, enema, elixir, syrup, emulsion, film, granule, gum, insert, jelly, foam, paste, pastille, pellet, spray, troche, lozenge, disk, magma, poultice, or wafer and the like.

As used herein, "immediate release" is used to describe a release profile to effect the delivery of an active as soon as possible, that is, as soon as practically made available to a subject, whether in active form, as a precursor and/or as a metabolite. Immediate release may also be defined functionally as the release of over 80 to 90 percent (%) of the active ingredient within about 60, 90, 100 or 120 minutes or less. Immediate release as used herein may also be defined as making the active ingredient available to the subject regardless of uptake, as some drugs may never be absorbed by the animal. Immediate release formulations of the active on a carrier, such as rolled or compressed beads, may be formulated such that the surface area is maximized on beads and the active is exposed immediately. Various immediate release active dosage forms may be designed readily by one of skill in art to achieve drug delivery to the stomach and small intestine, depending upon the choice of compression, adhesive materials and/or beading.

As used herein, the term "equilibrating," or "equilibration," refers to an exchange of anions or cations bonded to an ion exchange resin with the ions in a solution such that at least some of ions in the solution become ionically attached to the resin and such that at least some of the anions or cations bonded to the resin become dissolved in the solution. Equillibration is typically done with a solution containing oppositely charged ionic species. In the present invention, the ion originally in the solution that becomes bonded to the resin is typically a drug. The equilibrating step continues until an equilibrium is established between the exchange of the ions and although exchange continues, the net amount of each type of ion bonded to resin and dissolved in solution no longer changes.

As used herein, the term "coating" refers to the application of particles such as drug particles or membrane particles, onto the surface of the resin such that the particles adhere to the surface of the resin by forces that are non-ionic. In some embodiments, the coating is by a spray of a liquid containing the particles onto the resin as the liquid is being evaporated.

"Loading" refers to applying the drug molecule to an ion exchange resin and includes loading and/or equilibration.

As used herein, "extended release," "controlled release" and "delayed release" are used to define a release profile to effect delivery of an active over an extended period of time, defined herein as being between about 60 minutes and about 2, 4, 6 or even 24 hours. Extended release may also be defined functionally as the release of over 80 to 90 percent (%) of the active ingredient after about 60 minutes and about 2, 4, 6 or even 8 hours. Extended release as used herein may also be defined as making the active ingredient available to the subject regardless of uptake, as some drugs may never be absorbed by the subject. Various extended and delayed release dosage forms may be designed readily by one of skill in art as disclosed herein to achieve delivery to both the small and large intestines, to only the small intestine, or to only the large intestine, depending upon the choice of coating materials and/or coating thickness. As used herein, "a subject" is a patient, animal, insect, mammal or human, who will benefit from the method of this invention.

As used herein, a first active agent, a second active agent, two or more active agents individually include bioactive agents, pharmaceuticals, pharmaceuticals drugs, bioactive synthetic organic molecules, genetic materials, proteins, peptides, polypeptides, vitamins, steroids, genetic material, and diagnostic agents. Bioactive vitamins, steroids, proteins, peptides and polypeptides can be of natural origin or synthetic. Suitable diagnostic agents include but are not limited to dyes and contrast agents for use in connection with magnetic resonance imaging, ultrasound or computed tomography of a patient. In addition, the pharmaceutically active drug may be any pesticide known to the skilled artisan for use in the extended release pesticide control of insects, rodents and other pests.

The terms, "compound," "drug," "active agent," or "drug compound," are used interchangeably herein.

In a first embodiment, the invention is a method of preparing a controlled release active agent-ion exchange resin composition. The method comprises the steps of loading an ion exchange resin with a first charged active agent to result in an active agent-ion exchange resin; and then coating the active agent-ion exchange resin with a second charged active agent. The second charged active agent is preferably of an opposite charge than the first charged active agent.

The first charged active agent is preferably loaded onto the ion exchange resin by equilibration. The loading of the first charged active agent onto the ion exchange resin includes mixing the ion exchange resin in a solution in the presence of the first charged active agent and allowing sufficient time for the first active agent to equilibrate on to the resin. During the mixing, the first charged active agent equilibrates with the ions present on the resin. The equilibrium redistribution allows the unbound active agent or the free active agent to redistribute itself in equilibrium. The equilibrium distribution allows the free active agent to be further taken up by the resin. The active agent-ion exchange resin thus formed is optionally filtered and dried. It is not necessary to wash the active agent-ion exchange resin. In some embodiments, the ion exchange resin that is equilibrated with the first charged active agent by suspending the ion exchange resin in a solution containing the first charged agent, is then separated from the solution to result in a filtrate and the ion exchange resin with equilibrated first charged active agent. The remaining first charged active agent in the filtrate of the solution is then coated back onto the ion exchange resin equilibrated with the first charged active agent. Exemplary methods of coating the active agent-ion exchange resin with the first charged active agent include, but are not limited to, fluid bed coating, spray coating etc.

Alternatively, the first charged active agent is loaded onto the ion exchange resin by equilibration and the second charged active agent is coated onto the active agent-ion exchange resin. Exemplary methods of coating the active agent-ion exchange resin with the second charged active agent include, but are not limited to, fluid bed coating, spray coating etc. Spray coating is a commonly used method of coating the second active agent and may be additionally combined with simultaneous drying. After the active agent-ion exchange resin is coated with the second charged active agent, the resin/fluid slurry is optionally filtered and dried. It is not necessary to wash the active agent-ionic exchange resin complex after the additions.

In yet another alternative, the controlled release active agent-ion exchange resin composition described in any of the three prior paragraphs is coated with a rate controlling membrane. Suitable rate controlling membranes include, but are not limited to, wax, a fatty alcohol, shellac, zein, polyvinylpyrrolidone, a water insoluble cellulose derivative, ethyl cellulose, a polymethacrylate, or methyl cellulose. A preferred rate controlling membrane is ethyl cellulose or methyl cellulose. The coating materials may be applied as a solution or suspension in an aqueous fluid or as a solution in organic solvents. The membrane coated controlled release active agent-ion exchange resin compositions described herein are referred to as "membrane coated controlled release compositions."

The release profile can be further modified by selection of active agents used, by ratio of each active agent to the other, by selection of the rate controlling membrane, by controlling the membrane thickness, by dissolution media and other parameters.

In another alternative, the membrane coated controlled release compositions are suspended in a pharmaceutically acceptable liquid. Typically, the liquid comprises the second charged agent dissolved or suspended therein. Suitable pharmaceutically acceptable liquids for suspending the membrane coated controlled release compositions are well known in the art. Syrups are commonly used for this purpose and optionally comprise the second charged agent dissolved or suspended therein. Typically, the syrup is a viscous liquid that contains the agent along with ingredients such as, but not limited to, water, sweetener, flavoring agent, coloring agent, etc.

In a second embodiment, the invention is a controlled release composition. The controlled release composition comprises a first charged active agent and a second charged active agent. The second charged active agent is of an opposite charge than the first charged active agent. The first charged active agent and the second charged active agent are coated with a rate controlling membrane.

The first charged active agent is coated with the second charged active agent. The coating refers to the application of the second charged active agent onto the surface of the first charged active agent. Alternatively, the first charged active agent and the second charged active agent form a substantially homogenous mixture. In yet another alternative, the second charged active agent is absorbed or adsorbed onto the first charged active agent. The absorption or adsorption includes, without limitation, adhesion of the second active agent onto the surface of the first active agent or permeation of the second active agent into the first active agent. The permeation may involve ionic bond formation between the ions of opposite charge between the first active agent and the second active agent. The first charged active agent and the second charged active agent, as defined in this paragraph, will be referred to herein as "first active agent-second active agent complex."

In another alternative, the composition further comprises a carrier onto which the first and the second charged active agents are loaded. An ion exchange resin is a preferred carrier. Suitable ion exchange resins are described herein. When the carrier is an ion exchange resin, the carrier is equilibrated with the first charged active agent. The equillibration of the first charged active agent onto the ion exchange resin includes mixing the ion exchange resin in a solution in the presence of the first charged active agent and allowing sufficient time for the first active agent to equilibrate on to the resin. During the mixing, the first charged active agent equilibrates with the ions present on the resin. The equilibrium redistribution allows the unbound active agent or the free active agent to redistribute itself in equilibrium. The equilibrium distribution allows the free active agent to be further taken up by the resin. The active agent-ion exchange resin thus formed is optionally filtered and dried. It is not necessary to wash the active agent-ion exchange resin complex after the additions. The first active agent-ion exchange resin is then coated with the second active agent using the methods as described above.

In yet another alternative, the controlled release active agent-ion exchange resin composition described in any of the three prior paragraphs is coated with a rate controlling membrane. Suitable rate controlling membranes include, but are not limited to, wax, a fatty alcohol, shellac, zein, polyvinylpyrrolidone, a water insoluble cellulose derivative, ethyl cellulose, a polymethacrylate, or methyl cellulose. A preferred rate controlling membrane is ethyl cellulose or methyl cellulose. The coating materials may be applied as a solution or suspension in an aqueous fluid or as a solution in organic solvents. These membrane coated controlled release active agent-ion exchange resin compositions described herein are also referred to herein as "membrane coated controlled release compositions".

In another alternative, the membrane coated controlled release compositions are suspended in a pharmaceutically acceptable liquid. Typically, the liquid comprises the second charged agent dissolved or suspended therein. Suitable pharmaceutically acceptable liquids include syrups which comprise the second charged agent dissolved or suspended therein. Typically, the syrup contains the agent along with ingredients such as, but not limited to, water, sweetener, flavoring agent, coloring agent, etc.

For the embodiments described above, the first charged active agent is phenylephrine and the second charged active agent is ibuprofen. Alternatively, the first charged active agent and the second charged active agent, respectively, are Ibuprofen with phenylephrine; Naproxen with phenylephrine; Ketoprofen with phenyl ephrine; Ibuprofen with acetaminophen; Naproxen with acetaminophen; Ketoprofen with acetaminophen; Ibuprofen with phenylpropanolamine; Naproxen with phenylpropanolamine; Ibuprofen with dextromethorphan; Naproxen with dextromethorphan; Ketoprofen with dextromethorphan; Ibuprofen with diphenhydramine; Naproxen with diphenhydramine; Ketoprofen with diphenhydramine; Ibuprofen with famotidine; Naproxen with famotidine; Ketoprofen with famotidine; Ibuprofen with cimetidine; Naproxen with cimetidine; Ketoprofen with cimetidine; Salicylic acid with antihistamine; acidic compound with antihistamine; acidic compound with amine compound; acidic compound with amide compound; Ibuprofen with morphine; Naproxen with morphine; Ketoprofen with morphine; Ibuprofen with opiates; Naproxen with opiates; Ketoprofen with opiates; acidic compound with morphine; acidic compound with buprenorphine; and acidic compound with opiates. The cationic ion exchange resin for any of the foregoing drug pairs can be any available resin, including the following (H=acid form, K=potassium form, Na=sodium form): Amberlite IR-20(H); Dow XYS-40010.00 (H); Tulsion 344 (Na); Amberlite IRC-50 (H); Tulsion 339 (K); Amberlite IRP-58 (K); Amberlite IRP-64 (H); Amberlite IRP-69 (Na) or Amberlite IRP-120 (H) The ratio of the first charged active agent relative to the second charged active agent in the entire formulation is generally not critical and can range, for example, from about 1:20 to about 1:0.5; or from about 1:15 to about 1:1; or from about 1:10 to about 1:2.

Alternatively, the ratio of the first active agent to the second active agent is less than about 1:20; or about 1:15; or about 1:10; or about 1:9; or about 1:8; or about 1:7; or about 1:6; or about 1:5; or about 1:4; or about 1:3; or about 1:2; or about 1:1; or about 1:0.75; or about 1:0.9. In another alternative, the ratio of the first active agent to the second active agent inside the rate controlling membrane is in a range of about 1:2 to about 1:1; or about 1:2 to about 1:0.9; or about 1:2 to about 1:0.8; or about 1:2 to about 1:0.75; or about 1:2 to about 1:0.7; or about 1:2 to about 1:0.6; or about 1:2 to about 1:0.5.

For example, the ratio of phenylephrine to ibuprofen is less than about 1:20; or about 1:15; or about 1:10; or about 1:9; or about 1:8; or about 1:7; or about 1:6; or about 1:5; or about 1:4; or about 1:3; or about 1:2; or about 1:1; or about 1:0.75; or about 1:0.9. Alternatively, the ratio of phenylephrine to ibuprofen inside the rate controlling membrane is in a range of about 1:2 to about 1:1; or about 1:2 to about 1:0.9; or about 1:2 to about 1:0.8; or about 1:2 to about 1:0.75; or about 1:2 to about 1:0.7; or about 1:2 to about 1:0.6; or about 1:2 to about 1:0.5.

In one example, the molar ratio of the first charged active agent and the second charged active agent is in a range of about 1:2 to 1:0.75. In another example, the first charged active agent and the second charged active agent is in a range of about 1:1 to 1:0.9. In one example, the total ratio of the first charged active agent and the second charged active agent in the formulation is in a range of about 1:15 to 1:5. In some embodiments, the excess of the second active agent in the formulation provides controlled release of the first active agent in a subject even when the first active agent is administered alone in later dosages.

As used here in a charged agent, a charged active agent, a first charged active agent, a second charged active agent, a first drug, or a second drug are used to mean an agent that has a charge on at least a portion of the agent, e.g., the charge may be an ionic charge, charged functional groups, and so forth. In addition, the charge may very in strength depending on the specific agent.

Suitable pharmaceutically active drugs include narcotic analgesics, (e.g., codeine, dihydrocodeine, hydromorphone, morphine, pentazocine and propoxyphene), sympathomimetics, (e.g., norephedrine and pseudoephedrine), antitussives, (e.g., dextromethorphan, gauifenesin), analgesics, (e.g., aspirin and tramadol), antiemetics, (e.g., metoclopramide), anticholinergics, (e.g., atropine, ipratropium bromide and scopolamine), muscle relaxants, (e.g., cyclobenzaprine and papaverine), bronchodilators, (e.g., salbutamol, terbutaline and theophylline), antibiotics, (e.g., amoxycillin, ampicillin, azlocillin, bacampicillin, cefamandole, cefonicid, cefotaxime, cefotetan, cefoxitin, ceftriaxone, mezlocillin and piperacillin), antidepressants, (e.g., bupropion, nomifensine, and nortriptyline), antiasthmatics, (e.g., cromolyn), antineoplastics, (e.g., tamoxifen), antiepileptics, (e.g., valproic acid and phenvtoin), cardiovascular agents, (e.g., propranolol) phenylephrine, and gauifenesin. Acid addition salts or if appropriate, alkali or alkaline earth metal salts of the above drugs would be particularly suitable for use in the present invention.

Specific examples of suitable pharmaceutically active drugs include but not limited to dehydrocholic acid, diflunisal, ethacrynic acid, fenoprofen, furosemide, gemfibrozil, ibuprofen, naproxen, phenyloin, probenecid, sulindac, theophylline, salicylic acid, acetylsalicylic acid, acetophenazine, amitriptyline, amphetamine, benztropine, biperiden, bromodiphenhydramine, brompheniramine, carbinoxamine, chlorcyclizine, chlorpheniramine, chlorphenoxamine, chlorpromazine, clemastine, clomiphene, clonidine, codeine, cyclizine, cyclobenzaprine, cyproheptadine, desipramine, desloratadine, dexbrompheniramine, dexchlorpheniramine, dextroamphetamine, dextromethorphan, dicyclomine, diphemanil, diphenhydramine, doxepin, doxylamine, ergotamine, fluphenazine, haloperidol, hydrocodone, hydroxychloroquine, hydroxyzine, hyoscyamine, imipramine, levopropoxyphene, loratadine, maprotiline, meclizine, mepenzolate, meperidine, mephentermine, mesoridazine, methadone, methdilazine, methscopolamine, methysergide, metoprolol, nortriptylene, noscapine, nylindrin, orphenadrine, papaverine, pentazocine, phendimetrazine, phentermine, phenylephrine, phenylpropanolamine, pyrilamine, tripelennamine, triprolidine, promazine, propoxyphene, propanolol, pseudoephedrine, pyrilamine, quinidine, scopolamine, dextromethorphan, chlorpheniramine, codeine, aminocaproic acid, aminosalicylic acid, hydromorphone, isoxsuprine, levorphanol, melphalan, morphine, nalidixic acid, paraminosalicylic acid and mixtures and combinations thereof.

Examples of acidic and basic drugs that may be used with the present invention include phenylpropanolamine (PPA), dextromethorphan, ephedrin, pseudoephedrine, paramino salicyclic acid, acetyl salicylic acid, phentermine (phenyl-tertiary-butyl-amine) and acetaminophen. The skilled artisan will recognize the variety of drugs and resins that may be used and the modifications to alter the polymer, copolymer, cross linking agent that may be used to alter the characteristics of the drug-resin complex. The pharmaceutically active compounds useful in the practice of the present invention include antihistamines, decongestants, antitussives and/or expectorants. Other drugs for use with the present invention include, but are not limited to non-steroidal anti-inflammatory drugs (NSAIDs) and other analgesic drugs, e.g., acetaminophen and phenacetin. These materials are incorporated into the immediate or controlled release formulations of the invention in amounts governed by the desired release characteristics of the material in such excipient base and such that conventional dosages comply with applicable FDA or other regulations. The drug may be loaded in a specific concentration to allow the specific release of the drug over a given time range. In general, the maximum concentration of bound drug may be in excess of about 60%; however, ranges between about 1% and about 50% are contemplated with the present invention.

Examples of active agents for use with the present invention include, but are not limited to, hormone products such as, vasopressin and oxytocin and their derivatives, glucagon and thyroid agents as iodine products and anti-thyroid agents; cardiovascular products as chelating agents and mercurial diuretics and cardiac glycosides; respiratory products as xanthine derivatives (theophylline and aminophylline); anti-infectives as aminoglycosides, antifungals (e.g., amphotericin), penicillin and cephalosporin antibiotics, antiviral agents (e.g., zidovudine, ribavirin, amantadine, vidarabine and acyclovir), antihelmintics, antimalarials, and antituberculous drugs; biologicals such as antibodies (e.g., antitoxins and antivenins), vaccine antigens (e.g., bacterial vaccines, viral vaccines, toxoids); antineoplastics (e.g., nitrosoureas, nitrogen mustards, antimetabolites (fluorouracil, hormones, progestins and estrogens agonists and/or antagonists); mitotic inhibitors (e.g., etoposide and/or vinca alkaloids), radiopharmaceuticals (e.g., radioactive iodine and phosphorus products); and interferon, hydroxyurea, procarbazine, dacarbazine, mitotane, asparaginase and cyclosporins, including mixtures and combinations thereof. Exemplary polyanionic agents include but are not limited to sulphated polysaccharides, negatively charged serum albumin and milk proteins, synthetic sulphated polymers, polymerized anionic surfactants, and polyphosphates.

Other suitable therapeutics include, but are not limited to: thrombolytic agents such as urokinase; coagulants such as thrombin; antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adsnine, mercaptopolylysine, vincristine, busulfan, chlorambucil, melphalan (e.g., PAM, L-PAM or phenylalanine mustard), mercaptop urine, mitotane, procarbazine hydrochloride dactinomycin (actinomycin D), daunorubicinhydro chloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase), erwinaasparaginase, etoposide (VP-16), interferon alpha-2a, interferon alpha-2b, teniposide (VM-26), vinblastine sulfate (VLB), vincristine sulfate, bleomycin, bleomycin sulfate, methotrexate, adriamycin, and arabinosyl; blood products such as parenteral iron, hemin; biological response modifiers such as muramyldipeptide, muramyltripeptide, microbial cell wall components, lymphokines (e.g., bacterial endotoxin such as lipopolysaccharide, macrophage activation factor), sub-units of bacteria (such as *Mycobacteria, Corynebacteria*), the synthetic dipeptide N-acetyl-muramyl-L-alanyl-D-isoglutamine; anti-fungalagents such as ketoconazole, nystatin, griseofulvin, flucytosine (5-fc), miconazole, amphotericin B, ricin, and beta-lactam antibiotics (e.g., penicillin, ampicillin, sulfazecin); hormones such as growth hormone, PDGF, EGF, CSF, GM-CSF, melanocyte stimulating hormone, estradiol, beclomethasone dipropionate, betamethasone, betamethasone acetate and betamethasone sodium phosphate, vetamethasonedisodiumphosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisoloneacetate, prednisolone sodium phosphate, prednisolone rebutate, prednisone, triamcinolone, triamcinolone acetonide, triamcinolone diacetate, triamcinolone hexacetonide and fludrocortisone acetate; vitamins such vitamin C, E, A, K, ascyanocobalamin, neinoic acid, retinoids and derivatives such as retinolpalmitate, and alpha-tocopherol(s); peptides (e.g., T cell epitopes such as MAGE, GAGE, DAGE, etc.); proteins, such as manganese super oxide dimutase, alcohol dehydrogenase, nitric oxide synthase; enzymes such as alkaline phosphatase; antiallergic agents such as amelexanox; anti-coagulation agents such as phenprocoumon and heparin; circulatory drugs such as propranolol; metabolic potentiators such asglutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), Ribavirin andvidarabine monohydrate (adenine arabinoside, ara-A); antianginals such asdiltiazem, nifedipine, verapamil, erythrityl tetranitrate, isosorbidedinitrate, nitroglycerin (glyceryl trinitrate) and pentaerythritoltetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as difunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and megluminc antimonatc; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocainehydrochloride, lidocaine hydrochloride, mepivacaine hydrochloride, procainehydrochloride and tetracaine hydrochloride; general anesthetics such asdroperidol, etomidate, fentanyl citrate with droperidol, ketaminehydrochloride, methohexital sodium and thiopental sodium; and radioactive particles or ions such as strontium, iodide rhenium and yttrium, and combinations and mixtures thereof.

As used herein, a rate controlling membrane includes coatings or diffusion barrier coating materials which can be any of the conventional synthetic or natural film-forming materials with diffusion barrier properties and with no inherent pharmacological or toxic properties. In general, the major components of the coating should be insoluble in, and permeable to, water. Alternatively, a water-soluble substance, such as methyl cellulose may be incorporated, to alter the permeability of the coating, or an acid-insoluble, base-soluble substance to act as an enteric coating may be used. The water-permeable diffusion barrier will generally include a water insoluble material such as a wax, a fatty alcohol, shellac, zein, polyvinylpyrrolidone, a water insoluble cellulose derivative, ethyl cellulose, a polymethacrylate, or methyl cellulose. The coating materials may be applied as a solution or suspension in an aqueous fluid or as a solution in organic solvents. In some instances, the present invention may include a water-permeable diffusion barrier in contact with at least a portion of the ionic pharmaceutically active drug in communication with an ionic exchange resin.

Another example of a coated particle of the present invention provides a selective, prolonged continuous release of pharmacologically active drugs, under conditions such as those encountered in the gastrointestinal tract by the application of a diffusion barrier coating to an ion exchange drug-resin complex treated with a solvating agent.

For example, a water-permeable, diffusion barrier coating materials can be any of the conventional synthetic or natural film-forming materials with diffusion barrier properties and with no inherent pharmacological or toxic properties. For example, ethylcellulose, a water insoluble film-forming agent, may be used as a diffusion barrier membrane material. A plasticizer, (e.g., Durkex 500 vegetable oil) may be used to improve the film forming characteristics of ethylcellulose and/or to alter the permeability characteristics of the film. The amount of coating used depends on the degree of drug release prolongation desired and is a function of particle size, drug solubility, film permeability and other factors. By varying the amount of coating, and/or by blending coated drug-resin complex with uncoated drug-resin complex, and/or blending different coatings it is possible to selectively modify the preparation's drug dissolution profile as desired.

The manufacture of a formulation of any drug for liquid dosage usage requires that the final formulation have the drug dissolved or suspended in a liquid that possess extended shelf-life stability and exhibit no change in active drug dosage level over a period of time and has acceptable taste. Thus, to prepare a liquid formulation of any type drug it may be necessary to employ extenders such as water or syrup and to add flavors, sweeteners, thickening agents, dyes and the like. To control the dissolution profile of the formulation versus the dissolution profile of the same drug in water, the coated particles may also be included in the presence of ionic substances bearing the same ionic charge as the sustained release drug present in the formulation as a coated drug-resin complex. The second ionic material need not be coated with the water-permeable diffusion barrier coating.

As used herein, resin, carrier, carrier particle and ion exchange resin are used to describe various substrates that may be used with the present invention. For example, the cationic exchange resin of the present may be strongly or weekly acidic and have a variety of functional groups, e.g., weakly acidic type of resin containing carboxylic acid group, or strongly acidic type of resins containing sulfonic functional groups. Generally, the carboxylic functional groups are derived from polymers or copolymers of methacrylic acid or polymethacrylic acid and the sulfonic functional groups are generally derived from polymers or copolymers of styrene and divinylbenzene. Other polymeric matrices, organic ion exchange matrices or inorganic ion exchange matrices may be used as suitable ion exchange resins, e.g., methacrylic, acrylic and phenol formaldehyde.

Similarly, a wide range of cationic exchange resins or anionic exchange resins can be used to form ion exchange resin drug complexes. In general, ion-exchangers suitable for use in ion-exchange chromatography and for such applications as deionization of water are suitable for use as controlled release drug preparations. For examples, a model large ion exchange particle includes the cationic exchange resin Amberlite® IR-120 having a 20-30 mesh spherical particles and a model small ion exchange particle resin includes Amberlite® XE-69 with a 100-200 mesh fractured resin particles of Amberlite IR-120. The parent resin of Amberlite® IR-120 and Amberlite® XE-69 is described by the manufacturer as gel-type divinylbenzene sulfonic acid cation exchange resin that swells in water. Other suitable ion exchange resin candidates include synthetic ion exchange resins with different polymeric matrices (e.g., methacrylic, acrylic, phenol formaldehyde), ion exchange agents with cellulosic or dextran polymer matrices and inorganic ion exchange matrices.

In addition, ion exchange agents may be used in conjunction with polymer matrices (e.g., cellulosic or dextran) to form a suitable ion exchange resin. In one embodiment of the present invention, the ionic exchange resin is a sulfonic acid cationic exchange resin. The present invention also uses a sulphonic acid cation exchange resin, which includes phenol-sulphonic acid cation exchange resins and carboxylic-sulphonic acid cation exchange resins. Generally, the resin salt is obtained from the reaction of a sulphonic acid with an alkali, e.g., amine. The basic sulphonic acid cation exchange resin has a cation of an amphetamine adsorbed thereon. The skilled artisan will recognize that other cationic exchange resins may be used.

The ionic exchange resin includes sulfonic acid cationic exchange resin and may be made from a polyester polymer containing sulphonic groups, additionally containing units derived from ethylene glycol, units derived from tri- and tetraethylene glycol and units derived from terephthalate, neutralized polyesters having a terminal amine functional group, polyester block copolymers, block copolymers of phthalic and sulphonphthalic acid/ethylene glycol/polymethyl siloxane $\alpha$, $\gamma$-hydroxypropyl and vinyl acetate/vinyl butylbenzoate/crotonic acid. In addition, the polymer resin may be crosslinked. The crosslinkers include poly(2-acrylamido-2-methylpropanesulphonic acid) polymer with one monomer containing at least two olefinic double bonds, e.g., dipropylene glycol diallyl ether, polyglycol diallyl ether, triethylene glycol divinyl ether, hydroquinone diallyl ether, tetraallyloxyethanoyl, allyl ether, vinyl ether, a polyfunctional alcohol, tetraethylene glycol diacrylate, triallylamine, trimethylolpropane diallyl ether, methylenebisacrylamide or divinylbenzene.

Representative pharmaceutical grade ion exchange resins for use in accordance with the present invention are known to those skilled in the art. For example, pharmaceutical grade ion exchange resins are commercially available, e.g., the Rohm and Haas company and Dow Corning, e.g., Amberlite® IR-20, Amberlite® IRP-69, Amberlite® IRP-64, Amberlite® IRP-58, Amberlite® IRC-50, Amberlite® IRP-69 and Dow® XYS-40010.00, Dow® XYS-40013.00, etc. The pharmaceutical grade cationic ion-exchange resins may include particles of varying size ranges, and as either a monodisperse or a polydisperse mixture. The ion exchange resin particles may range in size from 40 to 1500. In one example, the gel-type divinylbenzene sulfonic acid cation exchange resin Amberlite® IRP-69 consisting of 100-200 mesh was used.

The present invention may be incorporated into a pharmaceutical composition and include immediate release, extended release or delayed release compositions. For example, the present invention provides compositions and methods for a modified-release pharmaceutical drug composition having a first charged active agent and a second charged active agent at least partially or completely surrounded, coated or encapsulated by a rate controlling membrane. The first charged active agent and the second charged active agent interact to form a modified release pharmaceutical complex within the rate controlling membrane and the modified release pharmaceutical complex has a release characteristic different from the release characteristic of the first active agent or the second active agent alone.

The skilled artisan understands that the first charged active agent, the second charged active agent or both may have an ionic charge, charged functional groups, and so forth. In addition, the first charged active agent and the second charged active agent may not have the same type of charge or number of charges. When a rate controlling membrane is included in the embodiment the skilled artisan will understand that a variety of membranes may be used to accomplish the protection. Common membrane materials include a wax, a fatty alcohol, a shellac, a zein, a polyvinylpyrrolidone, a water insoluble cellulose derivative, an ethyl cellulose, a polymethacrylate, a methyl cellulose or a combination thereof. The skilled artisan will understand that a variety of methods may be used to apply the coatings, e.g., by granulation, by physical mixing, by adsorption or a variety of other known methods.

The present invention also provides a method of preparing a modified-release pharmaceutical drug composition by combining a first charged active agent and a second charged active agent to form a modified release pharmaceutical complex with a release characteristic different from the release characteristic of the first active agent or the second active agent alone and coating the modified release pharmaceutical complex with a rate controlling membrane, wherein the modified release pharmaceutical complex is formed within the rate controlling membrane.

The skilled artisan will understand that a variety of the modified-release pharmaceutical drug composition may be formed in a number of manners including coating the second charged active agent onto the first charged active agent; loading the first charged active agent onto a first carrier, loading the second charged active agent onto a second carrier, and combining the first carrier and the second carrier; and/or combinations thereof.

The present invention may be incorporated into a pharmaceutical composition and include immediate release, extended release or delayed release compositions. The present invention relates to oral administration of cationic exchange resin drug complex, although other delivery methods are also contemplated, e.g., topical, rectal, injectable, subcutaneous, vaginal or nasal administration. The pharmaceutical compositions of the present invention can take the form of tablets, powders, capsules, gels, hydro-gels, solids, lyophilized suspensions, liquid suspensions or other conventional dosage forms. The present pharmaceutical composition may also be provided in a variety of dosage forms, e.g., solution, suspension, cream, ointment, lotion, capsule, caplet, softgel, gelcap, suppository, enema, elixir, syrup, emulsion, film, granule, gum, insert, jelly, foam, paste, pastille, pellet, spray, troche, lozenge, disk, magma, poultice, or wafer and the like. In addition the resin-drug complex of the present invention is suitable for dosages varying over a wide range, e.g., from about 0.01 to about 2000 mg, depending on the nature of the drug, resin and its intended usage.

The present invention includes two or more active agents within a rate controlling membrane, wherein the interaction between the two or more active agents form a complex within the rate controlling membrane. For example, a complex between a first active agent and a resin can be treated with a second active agent and subsequently coated with a rate controlling membrane.

In another example, a first active agent can be treated with a second active agent to form a complex that can then be subsequently coated with at rate controlling membrane. The skilled artisan will recognize that the second active agent may be coated onto the first active agent by coating, granulation, by physical mixing, by adsorption or a variety of other known methods.

Still another example, a first active agent and a second active agent may be loaded separately or jointly, onto a carrier particle and then be subsequently coated with at rate controlling membrane. In one example, the carrier particle is also an ion exchange resin capable of binding at least one of the active agents of interest, so that the release rate and release profile are modified in a manner different than that achieved when the carrier particle does not have ion exchange properties.

In one embodiment of the present invention, the modified complex is formed upon exposure to a liquid media. The modified complex may not form until a liquid media is present in sufficient amounts to allow one or more of the first active agent, the second active agent, the two or more active agents and/or the active agents to migrate or orientate themselves for interaction to occur. The modified complex achieves a thermal and/or chemical equilibrium and is generally stable once formed. The modified complex is formed within the rate controlling membrane so that the rate of release may be modulated by the membrane and controlled release products prepared.

In addition, the skilled artisan will recognize that the actual release profile may be modified by selection of compounds used, by ratio of each compound to the other, by selection of the rate controlling membrane and controlling the membrane thickness, by dissolution media and other parameters.

For example, the present invention may be used on a variety of different compositions including syrups, solids, liquids, gels, capsules, etc. In addition the present invention may be used in conjunction with other pharmaceutical preparations.

Preparation of Ion Exchange Sustained Release Phenylephrine Using the Technique Disclosed in U.S. Pat. Nos. 4,221,778 and 4,847,077, Modified by Procedures Disclosed in U.S. Publication No. 2007-0140983. Detailed Procedures are Described Below.

Preparation of Drug Loaded Ion Exchange Resin:

The following were placed into a 2 L stainless steel container and stirred for 5 hours:
 751.6 grams purified water
 251.5 grams sorbitol 70%
 300.5 grams ion exchange resin Amberlite IRP-69
 100.1 grams phenylephrine hydrochloride When mixing was complete the contents were filtered using Buchner filters. The filtrate was reserved and the filter cake was oven dried at 37° C. overnight. Samples were reserved for testing. Drying of the filter cake was then completed by placing 484.8 grams of the near dry filter cake into a fluid bed unit for about 15 minutes. After drying in the fluid bed Wurster Coating Unit, the reserved filtrate was applied as a coating onto the dried filter cake. Air flow, air temperature and spray rate were adjusted to avoid overwetting the product. Samples were again reserved.

Coating of Drug Loaded Ion Exchange Resin:

505 grams of the resin with filtrate applied were placed into the Wurster Fluid Bed Coating Unit and coated with a sustained release film composed of ethylcellulose plasticized with dibutyl sebacate (solvents were methanol and acetone). When 40% coating level (60% core/40% coating) was achieved, the process was terminated. Samples were again reserved.

The resulting product was a dry small particle formulation with the following release profile when tested using USP Apparatus 2.

| Time | % Release |
|---|---|
| 0.5 hours | 27.5% |
| 1.0 | 31.5% |
| 3.0 | 53.0% |
| 6.0 | 72.5% |
| 8.0 | 88.0% |

When formulated into syrup base, this product yielded the profiles of Column 1 and Column 2 of Table 1 below. In Column 2, the syrup contains Ibuprofen (100 mg of ibuprofen per 5 ml of syrup).

TABLE 1

| | Coated Phenylephrine/ Resin Complex Without free Ibuprofen | Coated Phenylephrine/ Resin Complex in presence of free Ibuprofen | Coated Phenylephrine/Resin/Ibuprofen Complex inside membrane in presence of free Ibuprofen |
|---|---|---|---|
| 0.5 hr | 37.2% | 83.6% | 55.8% |
| 1 hr | 41.0% | 92.0% | 63.2% |
| 3 hr | 49.2% | 100.3% | 82.6% |
| 6 hr | 56.2% | 100.6% | 90.0% |

The dose dumping observed in Column 2 of Table 1 indicates a further need to devise a shelf stable product which will maintain its sustained release character. Efforts to prevent the interaction of phenylephrine and ibuprofen proved inefficient and expensive. One approach was to apply an enteric coating that completely prevented water from permeating the sustained release coated ion exchange particles. This showed promise but the extra enteric coating was both expensive and increased the particle size of the coated ion exchange resin resulting in a product with poor mouth feel. Other coatings tried were either ineffective or had similar problems.

Formation and Loading of Ion Pair Complex:

An ion pair complex was prepared by placing an acidic drug and a basic drug into aqueous suspension/solution and stirring to allow the spontaneous formation of the complexed product.

A 1 L stainless steel container was charged with
400 grams purified water
120 grams phenylephrine hydrochloride
132 grams ibuprofen
(note: this is slightly greater than 1:1 mole ratio with a slight excess of ibuprofen)

The contents were stirred for 1 hour to allow spontaneous interaction to occur. The above mixture was added to 300 grams Puredent B730 (Grain Processing), an inert porous starch carrier, and mixed until the liquid was absorbed. The wet mass was then dried in a Wurster Fluid Bed Unit until just damp, then passed through an 18 U.S. Mesh screen to break up lumps, then further dried until free flowing. The dry free flowing product was then screened through a 50 U.S. Mesh screen to yield a powder of small particle size.

After screening and sampling, 308 grams of the material that passed through the 50 U.S. Mesh screen was charged into a Wurster Fluid Bed Coating Unit and was coated 40% coating level with Ethylcellulose plasticized with dibutylsebacate. Intermediate samples were taken at 30% and 35% coating levels.

This product, at 40% coating level, was then placed into an aqueous suspension to simulate syrup and was evaluated for sustained release. It was evaluated as the sole active in suspension and because more ibuprofen was required to provide proportional dosing, in the presence of the appropriate amount of additional free ibuprofen. These results are in Table 2, column 1 being the above product in aqueous suspension and column 2 being the same product in suspension with additional ibuprofen (89 mg ibuprofen suspended per 5 ml of the syrup). It is clear that the presence of free ibuprofen defeats the intended sustained release properties.

TABLE 2

| (Media = water) | Release of Phenylephrine From Encapsulated Phenyl/ Ibuprofen Complex absent Free Ibuprofen | Release of Phenylephrine From Encapsulated Phenyl/ Ibuprofen Complex in presence of Free Ibuprofen |
|---|---|---|
| 1.0 hr | 5.8% | 29.4% |
| 2.0 hr | 17.4% | 91.6% |
| 4.0 hr | 49.1% | |
| 8.0 hr | 68.7% | |
| 16 hr | 85.5% | |

Preparation of Successful Product:

Preparation of Drug Resin Complex and Filtrate Addition:

A 918 grams Purified Water was placed into a 2 L stainless steel container. While stirring, following was added:
83 grams sorbitol 70%
375 grams ion exchange resin Amberlite IRP-69
150 grams phenylephrine hydrochloride After additions were completed, the mixture was stirred for 4 hours. When stirring was complete the suspension was filtered using a Buchner filter. The filtrate (695 grams) was reserved and the filtered solids (839 grams) were dried in a Wurster Fluid Bed Coating Unit (dry weight 441 grams). After drying, the product was screened through a 50 U.S. Mesh sieve. The screened dry material was returned to the Wurster unit and the filtrate was spray applied onto it using air temperature and volume and a spray rate appropriate to maintain discrete particles and avoid agglomeration.

Ibuprofen Addition:

When filtrate application was complete an additional coating was prepared containing ibuprofen suspended in water with a starch binder (Capsul TA, National Starch). This suspension was prepared in a 1 L stainless steel container as follows.

To container was added 285 grams Purified Water. While stirring, 190 grams Capsul TA was added. While stirring, the solution was heated to 80° C., then allowed to cool. When cooled, 165 grams Ibuprofen was added. Stirring was continued until a uniform suspension was achieved.

This suspension was then coated onto the ion exchange resin which already had filtrate coated onto it. No effort was made to ionically bond either the phenylephrine in the filtrate or the ibuprofen in suspension with each other or with the ion exchange resin.

Coating of Ion Exchange Resin Loaded with Phenylephrine and Ibuprofen:

The drug loaded ion exchange resin containing both bound and free phenylephrine and free ibuprofen was then coated to 40% coating level with using ethylcellulose plasticized with dibutyl sebacate. Samples were removed at 30% and 35% coating levels.

This product was then formulated into a syrup preparation containing additional free ibuprofen (89 mg ibuprofen suspended per 5 ml of the syrup) to constitute appropriate levels of both drugs for a combination pharmaceutical product. This product has demonstrated satisfactory shelf stability retaining its sustained release phenylephrine profile for 9 months (when testing was discontinued). This data is in Table 1, column 3 and in the graph in the FIGURE.

As can be seen from these data, it was surprisingly found that by forming an ion pair between phenylephrine and ibuprofen within the controlled release rate controlling membrane, one could create a shelf stable product with the intended release profile.

Table 3 is an exemplary table of possible pharmaceutical compounds that may be used in conjunction with available resins. The skilled art will recognize that other compounds may be used with the present invention and that compounds may be modified or the particular chemical group modified in a compound to allow the use of that compound with the present invention.

TABLE 3

Pharmaceutical compounds and drug-resins:

| Pharmaceutical Compounds | Resins |
|---|---|
| Codeine, Dihydrocodeine, Hydromorphone, Morphine, Pentazocine and Propoxyphene Norephedrine and Pseudoephedrine Dextromethorphan, gauifenesin, phenylephrine Aspirin and Tramadol, naprisin Metoclopramide | Amberlite ® IR-20 |
| Atropine, Ipratropium Bromide and Scopolamine Cyclobenzaprine and Papaverine Salbutamol, Terbutaline and Theophylline | Amberlite ® IRC-50 |
| Amoxycillin, Ampicillin, Azlocillin, Bacampicillin, Cefamandole, Cefonicid, Cefotaxime, Cefotetan, Cefoxitin, Ceftriaxone, Mezlocillin and Piperacillin Bupropion, Nomifensine, and Nortriptyline Cromolyn | Amberlite ® IRP-58 |
| Valproic Acid and Phenvtoin Propranolol Tamoxifen Dehydrocholic Acid, Diflunisal, Ethacrynic Acid, Fenoprofen, Furosemide, Gemfibrozil, Ibuprofen, Naproxen, Phenytoin, Probenecid, Sulindac, Theophylline, Salicylic Acid, Acetylsalicylic Acid, | Amberlite ® IRP-64 |
| | Amberlite ® IRP-69 |
| Acetophenazine, Amitriptyline, Amphetamine, Benztropine, Biperiden, Bromodiphenhydramine, Brompheniramine, Carbinoxamine, Chlorcyclizine, Chlorpheniramine, Chlorphenoxamine, Chlorpromazine, Clemastine, Clomiphene, Clonidine, Codeine, Cyclizine, Cyclobenzaprine, Cyproheptadine, Desipramine, Dexbrompheniramine, Dexchlorpheniramine, Dextroamphetamine, Dicyclomine, Diphemanil, Diphenhydramine, Doxepin, Doxylamine, Ergotamine, Fluphenazine, Haloperidol, Hydrocodone, Hydroxychloroquine, Hydroxyzine, Hyoscyamine, Imipramine, Levopropoxyphene, Maprotiline, Meclizine, Mepenzolate, Meperidine, Mephentermine, Mesoridazine, Methadone, Methdilazine, Methscopolamine, Methysergide, Metoprolol, Nortriptylene, Noscapine, Nylindrin, Orphenadrine, Papaverine, Pentazocine, Phendimetrazine, Phentermine, Phenylpropanolamine, Pyrilamine, Tripelennamine, Triprolidine, Promazine, Propoxyphene, Propanolol, Pseudoephedrine, Pyrilamine, Quinidine, Scopolamine, Chlorpheniramine, Codeine, | Amberlite ® XE-69 |
| | Amberlite ® IR-120 |
| | Dow ® XYS-40013.00 |
| Aminocaproic Acid, Aminosalicylic Acid, Hydromorphone, Isoxsuprine, Levorphanol, Melphalan, Morphine, Nalidixic Acid, Paraaminosalicylic Acid Phenylpropanolamine (PPA), Dextromethorphan, Ephedrin, Pseudoephedrine, Paraamino Salicyclic Acid, Acetyl Salicylic Acid, Phentermine (Phenyl-Tertiary-Butyl-Amine) and Acetaminophen Acetominophen and Phenacetin | Dow ® XYS-40010.00 |

In addition the present invention may include other additives conventionally used in pharmaceutical compositions and known to those of skill in the art, e.g., anti-adherents, anti-sticking agents, glidants, flow promoters, lubricants, talc, magnesium stearate, fumed silica), micronized silica, surfactants, waxes, stearic acid, stearic acid salts, stearic acid derivatives, starch, hydrogenated vegetable oils, sodium benzoate, sodium acetate, leucine and magnesium lauryl sulfate.

In one embodiment, to prepare the coated pharmaceutical composition-resin complex, the pharmaceutical composition is dissolved in a suitable solvent or suspended in a suitable vehicle. The solvent containing the pharmaceutical composition is applied directly to the resin. One common method of loading the pharmaceutical composition to the ion exchange resin is to dissolve the pharmaceutical composition in water and spray it onto the ion exchange resin in fluid-bed coating apparatus; however, any other method of loading may be used. The loaded pharmaceutical composition-resin complex may then be coated using any suitable membrane material (e.g., ethylcellulose or any other common coating material may be used) to control the flow rate.

Thermodynamically, the equilibrium is independent of the type or thickness or even the presence of the coating, and dependent upon the ionic resin and the active agents e.g., the properties of the pharmaceutical composition itself and the proportions of pharmaceutical composition, the ion exchange sites of the ion exchange resin and any competing species. Thus when placed into an aqueous, non-ionic media (e.g., water or syrup base) the pharmaceutical composition will equilibrate with a substantial portion of the pharmaceutical composition bound to the ion resin and another portion free in the media. When competing ions are introduced, the pharmaceutical composition is displaced from the ion exchange resin.

In addition to pharmaceutical compounds used in conjunction with available resins the inventors have contemplated the use of other known active compounds with the present invention, e.g., herbicides, fungicides, insecticides, acaricides, nematicides, bird repellants, plant nutrients and agents that improve soil structure.

Examples of the insecticide, acaricide and nematocide that may be used with the present invention include pyrethroid compounds (e.g., permethrin, cypermethrin, fenvarelate, esfenvarelate, fenpropathrin, biphenthrin, deltamethrin, fluvalinate, flucythrinate, allethrin, d-allethrin, prallethrin, cyphenothrin, phenothrin, resmethrin, tefluthrin, empenthrin, acrinathrin, cyhalothrin, cyfluthrin, etofenprox, halfenprox, silafluofen, tralomethrin, cycloprothrin, esbiothrin, transfluthrin, terallethrin, imiprothrin and 1-ethynyl-2-fluoro-2-pentenyl 3-(2,2-dichlorovinyl)-2,2-dimethylcyclopropanecarboxylate); organophosphorus compounds (e.g., cyanophos, fenthion, fenitrothion, parathion, methylparathion, pirimiphos-methyl, diazinon, isoxathion, pyridaphenthion, chlorpyrifos, chlorpyrifos-methyl, oxydeprofos, vamidothion, malathion, phenthoate, dimethoate, thiometon, disulfoton, phosalone, phosmet, methidathion, prothiofos, sulprofos, profenofos, azinphosmethyl, pyraclofos, salithion, tetrachlorvinphos, dichlorvos, monocrotophos, naled, dimethylvinphos, propaphos, acephate, metamidofos and ethion; carbamate compounds such as carbaryl, metolcarb, isoprocarb, fenobcarb, propoxur, XMC, ethiofencarb, bendiocarb, pyrimicarb, carbosulfan, carbofuran, benfuracarb, furathiocarb, methomyl, thiodicarb, oxamyl, alanycarb, metoxadiazone and fenothiocarb); neonicotinoids (e.g., nitroiminoimidazolidine derivatives, nitrovinylidenediamine derivatives (e.g. N-[(6-chloro-3-pyridylmethyl)-N-ethyl-N'-methyl-2-nitrovinylidenediamine (common name: nitenpyram)], nitroguanidine derivatives, cyano acetamidine derivatives, N1-[(6-chloro-3-pyridyl)methyl]-N2-cyano-N1-methylacetamidine, cyanoiminothiazolidine derivatives, 1-(2-chloro-5-pyridylmethyl)-2-cyanoiminothiazolidine, nitroiminotetrahydro-1,3,5-oxadiazine derivatives, 3-[(2-chloro-5-thiazolyl)methyl]-5-methyl-4-nitroiminotetrahydro-1,3,5-oxadiazine (common name: thiamethoxam), nitroiminohexahydro-1,3,5-triazine derivatives, 3,5-dimethyl-1-[(2-chloro-5-thiazolyl)methyl]-2-nitroiminohexahydro-1,3,5-triazine); nereistoxin derivatives (e.g., cartap, bensultap and thiocyclam); chlorinated hydrocarbon compounds (e.g., benzoepin, dicofol and tetradifon; formamidine derivatives (e.g., amitraz and chlordimeform); phenylpyrazole derivatives (e.g., ethiprole); benzoylphenylurea compounds (e.g., diflubenzuron, teflubenzuron, chlorfluazuron, flufenoxuron, triflumuron, hexaflumuron, lufenuron and novaluron); triazine derivatives (e.g., cyromazine); thiadiazine derivatives (e.g., buprofezine); juvenoid compounds (e.g., methoprene, hydroprene, fenoxycarb and diofenolan); tebufenozide; methoxyfenozide; halofenozide; chromafenozide; chlorofenapir; phenisobromolate; quinomethionate; prop argit; fenbutatin oxide; hexythiazox; etoxazole; clofentezine; fenpyroximate; tebufenpyrad; pyrimidifen; polynactin complex; milbemectin; avermectin; ivermectin and azadirachtin.

Specific examples of a insecticides include: 2,3,5,6-tetrafluorobenzyl-chrysanthemate; 2,3,5,6-tetrafluorobenzyl-2,2-dimethyl-3-(1-propenyl)cyclopropane carboxylate; 4-methyl-2,3,5,6-tetrafluorobenzyl-chrysanthemate; 4-methyl-2,3,5,6-tetrafluorobenzyl-2,2-dimethyl-3-(2,2-dichlorovinyl) cyclopropane carboxylate; 4-methyl-2,3,5,6-tetrafluorobenzyl-2,2-dimethyl-3-(2,2-difluorovinyl) cyclopropane carboxylate; 4-methoxymethyl-2,3,5,6-tetrafluorobenzyl-chrysanthemate; 4-methoxymethyl-2,3,5,6-tetrafluorobenzyl-2,2-dimethyl-3-(1-propenyl) cyclopropane carboxylate; 2,3,4,5,6-pentafluorobenzyl-2,2-dimethyl-3-(2-chloro-2-trifluoromethylvinyl)cyclopropane carboxylate; and 4-propargyl-2,3,5,6-tetrafluorobenzyl-3-(1-propenyl)-2,2-dimethylcyclopropane carboxylate. Further, as examples of compounds other than those expressed by formula (I), the following chemicals may be given: 4-methoxymethyl-2,3,5,6-tetrafluorobenzyl-2,2,3,3-tetramethylcyclopropane carboxylate; and 4-propargyl-2,3,5,6-tetrafluorobenzyl-2,2,3,3-tetramethylcyclopropane carboxylate.

Suitable herbicides include: anilides (e.g., diflufenican and propanil), arylcarboxylic acids (e.g., dichloropicolinic acid, dicamba and picloram), aryloxyalkanoic acids (e.g., 2,4-D, 2,4-DB, 2,4-DP, fluoroxypyr, MCPA, MCPP and triclopyr), aryloxy-phenoxy-alkanoic esters (e.g., diclofop-methyl, fenoxaprop-ethyl, fluazifop-butyl, haloxyfop-methyl and quizalofop-ethyl), azinones (e.g., chloridazon and norflurazon), carbamates (e.g., chlorpropham, desmedipham, phenmedipham and propham), chloroacetanilides (e.g., alachlor, acetochlor, butachlor, metazachlor, metolachlor, pretilachlor and propachlor), dinitroanilines (e.g., oryzalin, pendimethalin and trifluralin), diphenyl ethers (e.g., acifluorfen, bifenox, fluoroglycofen, fomesafen, halosafen, lactofen and oxyfluorfen), ureas (e.g., chlortoluron, diuron, fluometuron, isoproturon, linuron and methabenzthiazuron), hydroxylamines (e.g., alloxydim, clethodim, cycloxydim, sethoxydim and tralkoxydim), imidazolinones (e.g., imazethapyr, imazamethabenz, imazapyr and imazaquin), nitriles (e.g., bromoxynil, dichlobenil and ioxynil), oxyacetamides (e.g., mefenacet), sulphonylureas (e.g., amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl), thiocarbamates (e.g., butylate, cycloate, di-allate, EPTC, esprocarb, molinate, prosulfocarb, thiobencarb and tri-allate), triazines (e.g., atrazine, cyanazine, simazine, simetryne, terbutryne and terbutylazine), triazinones (e.g., hexazinone, metamitron and metribuzin), others (e.g., aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinclorac, quinmerac, sulphosate and tridiphane).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention.

All such similar substitutes and modifications apparent to those skilled in the art are deemed to be within the spirit, scope and concept of the invention as defined by the appended claims.

REFERENCES

1. Gelotte; U.S. Pat. No. 6,211,246; Rapidly Absorbed Liquid Compositions
2. Gelotte: U.S. Pat. No. 7,060,730; Rapidly Absorbed Liquid Compositions
3. Fawzi; U.S. Pat. No. 5,373,022; Salt/Ion Pairs of Non-steroidal Anti-inflammatory Drugs in Various Dosage Forms
4. Fawzi; U.S. Pat. No. 5,385,941; Salt/Ion Pairs of Non-steroidal Anti-inflammatory Drugs in Various Dosage Forms
5. Raghunathan; U.S. Pat. No. 4,221,778; Prolonged Release Pharmaceutical Preparations
6. Raghunathan; U.S. Pat. No. 4,847,077; Controlled Release Pharmaceutical Preparations
7. Rohm and Haas; New Uses of Ion Exchange Resins in Pharmaceutical Formulation; L. Hughes, Rohm & Haas Research Laboratories
8. Pharmaceutical Technology, 2004; Ion Exchange Resins— Unique Solutions to Formulation Problems; L. Hughes.

What is claimed is:

1. A controlled release composition, comprising phenylephrine/phenylephrine-HCl and ibuprofen,
    wherein the composition further comprises an ion exchange resin equilibrated with the phenylephrine/phenylephrine-HCl and the ion exchange resin equilibrated with the phenylephrine/phenylephrine-HCl is (i) coated with the ibuprofen or (ii) coated with phenylephrine/phenylephrine-HCl and ibuprofen, and
    wherein the ion exchange resin equilibrated with the phenylephrine/phenylephrine-HCl and (i) coated with the ibuprofen or (ii) coated with phenylephrine/phenylephrine-HCl and ibuprofen is further coated with a rate controlling membrane,
    wherein the composition is suspended in a pharmaceutically acceptable syrup and wherein the syrup further comprises ibuprofen dissolved or suspended therein.

2. The composition of claim 1, wherein a molar ratio of the phenylephrine/phenylephrine-HCl and the ibuprofen is in a range of about 1:2 to 1:0.75.

3. The composition of claim 1, wherein a molar ratio of the phenylephrine/phenylephrine-HCl and the ibuprofen is in a range of about 1:1 to 1:0.9.

4. A method of preparing a controlled release active agent-ion exchange resin composition, comprising:
    loading an ion exchange resin with phenylephrine or phenylephrine-HCl to result in an active agent-ion exchange resin such that the ion exchange resin is equilibrated with the phenylephrine or phenylephrine-HCl;
    coating the active agent-ion exchange resin with ibuprofen;
    coating the ion exchange resin loaded with the phenylephrine or phenylephrine-HCl and coated with the ibuprofen with a rate controlling membrane, and
    suspending the composition in a pharmaceutically acceptable syrup containing the ibuprofen dissolved or suspended therein.

5. The method of claim 4,
    wherein the phenylephrine or phenylephrine-HCl is loaded onto the ion exchange resin by equilibration; or
    wherein the ion exchange resin is equilibrated with the phenylephrine or phenylephrine-HCl by suspending the ion exchange resin in a solution containing the phenylephrine or phenylephrine-HCl, and wherein the ion exchange resin is then separated from the solution to result in a filtrate and the ion exchange resin equilibrated with the phenylephrine or phenylephrine-HCl; and wherein the remaining phenylephrine or phenylephrine-HCl in the filtrate of the solution is coated back onto the ion exchange resin equilibrated with the phenylephrine or phenylephrine-HCl.

6. The method of claim 5, wherein the phenylephrine or phenylephrine-HCl in the filtrate is coated onto the ion exchange resin by spray coating.

* * * * *